(12) United States Patent
Ogino et al.

(10) Patent No.: US 11,791,015 B2
(45) Date of Patent: Oct. 17, 2023

(54) ELECTROPHORESIS SEPARATION DATA ANALYZER

(71) Applicant: SHIMADZU CORPORATION, Kyoto (JP)

(72) Inventors: Kota Ogino, Kyoto (JP); Akira Harada, Kyoto (JP); Hidesato Kumagai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 686 days.

(21) Appl. No.: 16/705,348

(22) Filed: Dec. 6, 2019

(65) Prior Publication Data

US 2020/0211672 A1 Jul. 2, 2020

(30) Foreign Application Priority Data

Dec. 27, 2018 (JP) ................................ 2018-244082

(51) Int. Cl.
*G16B 15/00* (2019.01)

(52) U.S. Cl.
CPC ................... *G16B 15/00* (2019.02)

(58) Field of Classification Search
CPC ..................................................... G16B 15/00
USPC ........................................................... 702/19
See application file for complete search history.

(56) References Cited

U.S. PATENT DOCUMENTS

| 8,321,142 | B2 | 11/2012 | Odachi |
| 2010/0010748 | A1* | 1/2010 | Perlin ................. C12Q 1/6809 702/19 |
| 2018/0150616 | A1 | 5/2018 | Akamaru |

FOREIGN PATENT DOCUMENTS

| CN | 108120732 A | 6/2018 |
| JP | 11118760 A | 4/1999 |
| JP | 2008-241517 A | 10/2008 |
| JP | 4648250 B2 | 3/2011 |
| JP | 2012168014 A | 9/2012 |
| JP | 2018-025536 A | 2/2018 |

OTHER PUBLICATIONS

Office Action dated Feb. 8, 2022 issued by the Japanese Patent Office in Japanese Application No. 2018-244082.
Communication dated Jun. 17, 2021 by the Indian Patent Office in application No. 201944053257.
Communication dated Apr. 26, 2022 from the Chinese Patent Office in Chinese Application No. 201911377724.7
Office Action dated Jun. 17, 2023 in Chinese Application No. 201911377724.7.

* cited by examiner

*Primary Examiner* — Yih-Horng Shiao
(74) *Attorney, Agent, or Firm* — Sughrue Mion, PLLC

(57) ABSTRACT

An analyzer includes a separation data holding part, a determination criterion holding part, and a component peak determination part. The separation data holding part retains, as reference data, separation data obtained by an electrophoresis analysis for a reference sample including a reference component which is a known component and retains, as data to be analyzed, separation data obtained by an electrophoresis analysis for a sample to be analyzed. The determination criterion holding part retains a determination criterion for determining whether a component peak in the reference data and a component peak in the data to be analyzed are identical. The component peak determination part is configured to determine whether the component peak in the reference data and the component peak in the data to be analyzed are identical to each other, using the determination criterion.

11 Claims, 8 Drawing Sheets

FIG. 6

| FRAGMENT NAME | Sample1 | Sample2 | Sample3 |
|---|---|---|---|
| Fragment No.1 | ○ | ○ | |
| Fragment No.2 | ○ | | ○ |
| Fragment No.3 | | | ○ |
| Fragment No.4 | | | ○ |
| Fragment No.5 | | | |
| Fragment No.6 | | ○ | |
| Fragment No.7 | ○ | ○ | ○ |
| Fragment No.8 | ○ | | |
| Fragment No.9 | ○ | | |
| Fragment No.10 | ○ | ○ | ○ |
| Fragment No.11 | | | |
| Fragment No.12 | ○ | | ○ |
| Fragment No.13 | ○ | | ○ |
| Fragment No.14 | ○ | | ○ |
| Fragment No.15 | ○ | ○ | ○ |
| Fragment No.16 | ○ | ○ | ○ |
| Fragment No.17 | ○ | ○ | |
| Fragment No.18 | ○ | ○ | ○ |

FIG. 8

| FRAGMENT NAME | Sample1 | Sample2 | Sample3 |
|---|---|---|---|
| Fragment No.1 | ○ | ● | |
| Fragment No.2 | ○ | | ○ |
| Fragment No.3 | | | ○ |
| Fragment No.4 | | | ○ |
| Fragment No.5 | | | |
| Fragment No.6 | | ○ | |
| Fragment No.7 | ○ | ○ | ○ |
| Fragment No.8 | ○ | | |
| Fragment No.9 | ○ | | |
| Fragment No.10 | ○ | ○ | ○ |
| Fragment No.11 | | | |
| Fragment No.12 | ○ | | ○ |
| Fragment No.13 | ○ | | ○ |
| Fragment No.14 | ○ | | ○ |
| Fragment No.15 | ○ | ○ | ○ |
| Fragment No.16 | ○ | ○ | ○ |
| Fragment No.17 | ○ | ○ | |
| Fragment No.18 | ○ | ○ | ○ |

ELECTROPHORESIS SEPARATION DATA ANALYZER

BACKGROUND OF THE INVENTION

1. Field of the Invention

The present invention relates to an analyzer having a function of automatically performing a fingerprinting analysis of separation data obtained by an electrophoresis analysis.

2. Description of the Related Art

Known methods of analyzing separation data acquired by electrophoresis analysis include a fingerprinting analysis in which separation data for a reference sample containing known components (hereinafter referred to as reference data) is compared with separation data for a sample to be analyzed (hereinafter referred to as data to be analyzed), and the component contained in a sample to be analyzed is identified.

The fingerprinting analysis is generally performed by arranging reference data and data to be analyzed (or a gel image (arrangement of each component peak with a specific separation index (for example, fragment size) as an axis) created based on the above data side by side, and visually checking whether the component peak identical to each component peak on the reference data is present on the data to be analyzed.

CITATION LIST

Patent Literature

Patent Literature 1: JP 2018-025536 A

SUMMARY OF THE INVENTION

In electrophoresis analysis, even when the same substance is measured, separation data may vary. In particular, when electrophoresis is performed using a plurality of migration flow paths, the separation data tends to vary due to analysis errors between the migration paths. When the variation between the separation data is large, it becomes difficult to identify the component to be analyzed by comparing the reference data with the data to be analyzed.

In order to reduce the variation between the separation data, it has been proposed to correct the peak waveform of the data to be analyzed based on the reference data (see Patent Literature 1). The waveform correction of the data to be analyzed is performed by expanding/contracting or shifting the peak waveform in a specific range in the data to be analyzed in the time axis direction under a certain condition. This facilitates comparison between the reference data and the data to be analyzed.

However, in the conventional fingerprinting analysis, since the component in the sample to be analyzed is identified based on a visual determination, there is a concern that the results may vary depending on the user's subjectivity. Further, the visual determination by the user takes a long time, and there is a problem that human error is likely to occur.

Accordingly, an object of the present invention is to provide an analyzer having a function of automatically performing a fingerprinting analysis of separation data obtained by an electrophoresis analysis.

The present invention is an analyzer that analyzes separation data obtained by an electrophoresis analysis. The analyzer includes a separation data holding part, a determination criterion holding part, and a component peak determination part. The separation data holding part configured to hold, as reference data, separation data obtained by an electrophoresis analysis of a reference sample including reference components which are known components and to hold, as data to be analyzed, separation data obtained by an electrophoresis analysis of a sample to be analyzed. The determination criterion holding part configured to hold a determination criterion for determining whether component peaks in the reference data and component peaks in the data to be analyzed are identical. The component peak determination part is configured to determine whether the component peak in the reference data and the component peak in the data to be analyzed are identical respectively using the determination criterion.

In a preferred embodiment, the analyzer includes a component-to-be-analyzed index value identification part configured to identify, as a component-to-be-analyzed index values, separation index values of component peaks in the data to be analyzed, and a reference component index value identification part configured to identify, as reference component index values, separation index values of component peaks in the reference data, wherein the component peak determination part is configured to determine that the component peak in the reference data and the component peak in the data to be analyzed are identical to each other, when a difference between the reference component index value of the component peak in the reference data and the component-to-be-analyzed index value of the component peak in the data to be analyzed satisfies the determination criterion.

In the above case, the determination criterion may be a difference allowance ratio that is a ratio of a difference between the component-to-be-analyzed index value and the reference component index value to the reference component index value.

Further, the analyzer according to the present invention may have a function of performing waveform correction for expanding/contracting and/or shifting the peak waveform so that the peak waveform in a specific range in the data to be analyzed is matched with the peak waveform in the corresponding range in the reference data. That is, in a preferred embodiment of the analyzer according to the present invention further includes a waveform correction part configured to perform a waveform correction to expand/contract and/or shift a peak waveform in the analysis target range within a predetermined allowable range so that a correlation between a peak waveform in an analysis target range set in the data to be analyzed and a peak waveform in a range in the reference data corresponding to the analysis target range is maximized, wherein the component peak determination part is configured to determine, when a correlation between a peak waveform in the analysis target range after the waveform correction is performed and a peak waveform in a range in the reference data corresponding to the analysis target range satisfies the determination criterion, that component peaks in the analysis target range are identical to component peaks in the range in the reference data corresponding to the analysis target range. Note that the waveform correction is disclosed in detail in Patent Literature 1.

In the above case, the user may arbitrarily designate the analysis target range. That is, the analyzer may further include an analysis target range designation part configured to require a user to designate the analysis target range, wherein the waveform correction part may be configured to perform the waveform correction on the analysis target range designated by a user.

Further, the user may arbitrarily set the allowable range of waveform correction. That is, the analyzer may further include a correction allowable range designation part configured to require a user to designate the allowable range, wherein the waveform correction part may be configured to perform the waveform correction in the allowable range designated by a user.

Moreover, the analyzer may be configured in such a way that the user can arbitrarily set the determination criterion. That is, the analyzer may further include a determination criterion input part configured to require a user to input the determination criterion, wherein the determination criterion holding part may be configured to hold the determination criterion input by the user.

The separation data holding part may be configured to hold a plurality of pieces of separation data, to hold, as the reference data, one piece of the separation data, that is identified by a user, of the plurality of pieces of separation data, and to hold, as the data to be analyzed, at least one piece of the separation data of the remaining separation data.

Further, the analyzer may further include an index value designation part configured to require a user to designate, using a separation index value, a component peak to be determined whether it is in the data to be analyzed or not, wherein the component peak determination part may be configured to determine that component peak in the data to be analyzed is identical to a component peak designated by a user using the separation index value when a difference between the separation index value designated by the user and the component-to-be-analyzed index value of the component peak in the data to be analyzed satisfies the determination criterion. By such configuration, the user can designate the component peak to be determined whether it is in the analysis data or not using the separation index value.

Moreover, the analyzer may further include a reference component name input part configured to require a user to input names of the reference components.

Further, as above, the determination criterion includes a difference allowance ratio between the component peak separation index value in the data to be analyzed and the component peak separation index value in the reference data, and when such a determination criterion is set, the determination criteria for component peaks adjacent to each other in the reference data may overlap each other. In such a case, when the separation index value of the component peak in the data to be analyzed is within the overlapping range of determination criteria, the component peak is determined to be identical as a plurality of component peaks in the reference data, so that one component peak in the data to be analyzed is identified for a plurality of component peaks.

Therefore, when there is a plurality of component peaks, in the reference data, that is capable of being determined to be identical to a component peak in the data to be analyzed as a result of a determination using the determination criterion, the component peak determination part is configured to determine that one component peak, in the reference data, having a separation index value closest to a separation index value of the component peak in the data to be analyzed is identical to the component peak in the data to be analyzed. This can prevent one component peak in the data to be analyzed from being identified for a plurality of component peaks.

In the above case, when the component peak determination part determines that one component peak from among the plurality of component peaks, in the reference data, that is capable of being determined to be identical to a component peak in the data to be analyzed is identical to the component peak in the data to be analyzed, a determination result output part that outputs a determination result by the component peak determination part may be configured to issue a written warning in the determination result. Thus, the user can easily recognize that there is a plurality of component peaks in the reference data that can be determined to be identical to the component peaks in the data to be analyzed by the warning issued in the determination result.

The analyzer according to the present invention is configured to automatically determine whether the component peak in the data to be analyzed is identical to the component peak in the reference data using a preset determination criterion, so that it is possible to perform fingerprinting automatically, which was performed visually by a user before.

BRIEF DESCRIPTION OF THE DRAWINGS

FIG. 6 is a diagram showing another example (determination result table) of fingerprinting determination result data of in the embodiment;

FIG. 8 is a diagram showing another example (determination result table) of fingerprinting determination result data of the embodiment.

DETAILED DESCRIPTION OF THE INVENTION

Hereinafter, an embodiment of an analyzer that analyzes separation data obtained by electrophoresis analysis will be described with reference to the drawings.

Figure 1:
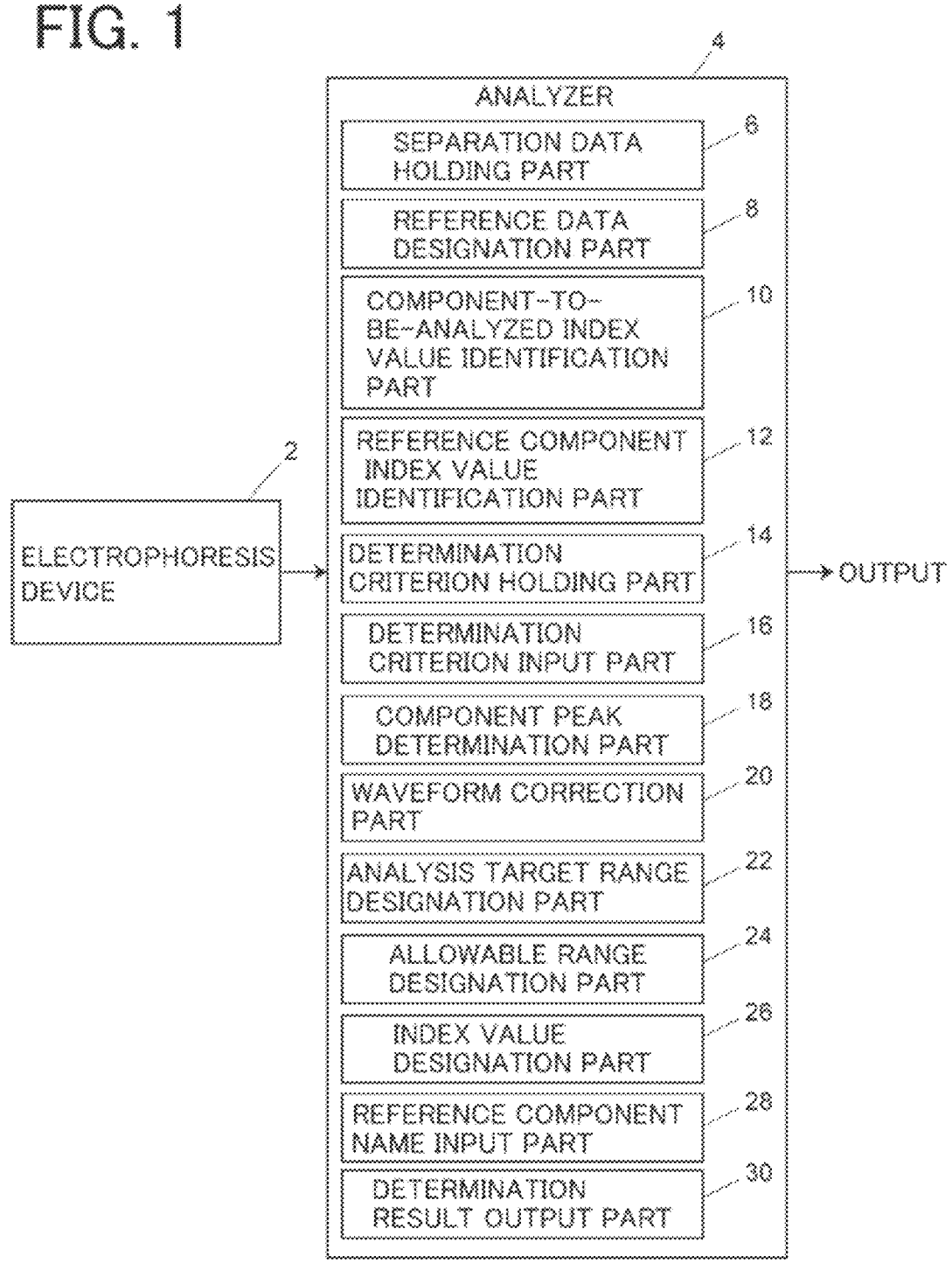
FIG. 1 is a block diagram schematically showing an embodiment of an analyzer.

As shown in FIG. 1, an analyzer 4 is realized by a computer that can communicate with an electrophoresis device 2. Separation data acquired by electrophoresis analysis in the electrophoresis device 2 is taken into the analyzer 4.

The analyzer 4 includes a separation data holding part 6, a reference data designation part 8, an component-to-be-analyzed index value identification part 10, a reference component index value identification part 12, a determination criterion holding part 14, a determination criterion input part 16, a component peak determination part 18, a waveform correction part 20, an analysis target range designation part 22, an allowable range designation part 24, an index value designation part 26, a reference component name input part 28, and a determination result output part 30. The separation data holding part 6 and the determination criterion holding part 14 are functions realized by a partial storage area of a storage device provided in a computer constituting the analyzer 4. The reference data designation part 8, the component-to-be-analyzed index value identification part 10, the reference component index value identification part 12, the determination criterion input part 16, the component peak determination part 18, the waveform correction part 20, the analysis target range designation part 22, the allowable range designation part 24, the index value designation part 26, the reference component name input part 28, and the determination result output part 30 are functions obtained by an arithmetic element such as a CPU provided in a computer constituting the analyzer 4 executing a program.

The separation data holding part 6 is a storage area that holds the separation data fetched from the electrophoresis device 2. Usually, in the electrophoresis device 2, an electrophoresis analysis is performed on a reference sample including a plurality of reference components that is known components and a sample including an unknown component, and each separation data is acquired and fetched into the analyzer 4.

In the analyzer 4, it is usually impossible to determine which separation data among the separation data fetched from the electrophoresis device 2 is separation data (reference data) for the reference sample. Therefore, the analyzer 4 includes the reference data designation part 8 configured to require the user to designate separation data to be handled as reference data from among a plurality of separation data fetched from the electrophoresis device 2 into the analyzer 4. The reference data designation part 8 can require the user to designate two or more pieces of separation data as reference data. The separation data holding part 6 is configured to hold the separation data designated by the user as reference data. The separation data other than the reference data fetched from the electrophoresis device 2 into the analyzer 4 is held in the separation data holding part 6 as data to be analyzed.

The component-to-be-analyzed index value identification part 10 is configured to identify the separation index value of each component peak in the data to be analyzed as the component-to-be-analyzed index value. The reference component index value identification part 12 is configured to identify the separation index value of each component peak in the reference data as the reference component index value. The separation index value is, for example, time or size.

The determination criterion holding part 14 is a storage area that holds a criterion for determining whether the component peak in the data to be analyzed is the component peak identical to the component peak in the reference data.

The determination criterion input part 16 is configured to require the user to input a determination criterion. The determination criterion input by the user is held in the determination criterion holding part 14. The determination criterion to be input by the user may be a value arbitrarily determined by the user, or may be a value selected by the user from a plurality of options. Further, the determination criterion held in the determination criterion holding part 14 is not necessarily input by the user, and a preset value may be used as the determination criterion.

The component peak determination part 18 is configured to determine whether the component peak in the data to be analyzed and the component peak in the reference data are identical to each other using the determination criterion held in the determination criterion holding part 14. In this embodiment, whether the component peak in the data to be analyzed and the component peak in the reference data are identical to each other is determined based on the separation index value of each component peak or based on the correlation between the component peaks. When the determination is performed based on the separation index value, the ratio (for example, ±5% of the reference component index value) of the difference between the component-to-be-analyzed index value of the component peak in the data to be analyzed and the reference component index value of the component peak in the reference data to the reference component index value can be set to the determination criterion. In this case, when the difference between the separation index values of the two component peaks to be compared is within a certain ratio (for example, 5%) of the reference component index value both component peaks can be determined as identical to each other. On the other hand, when the determination is performed based on the correlation between the component peaks to be compared, the threshold value of the correlation value between the component peaks to be compared can be provided as a determination criterion. In this case, when the correlation value exceeds the threshold value, the component peaks to be compared can be determined as identical to each other.

The waveform correction part 20 is configured to perform waveform correction to expand/contract and/or shift the specific range of the data to be analyzed so that the peak waveform within the specific range in the data to be analyzed is matched with the peak waveform within the specific range of the reference data. The waveform correction is performed in order to correct variations in separation data due to the difference in electrophoresis analysis conditions (such as flow paths) between the reference sample and the sample to be analyzed, and is disclosed in Patent Literature 1 (JP 2018-025536 A).

The detailed explanation here is omitted, but in the waveform correction, the specific range (analysis target range) in the data to be analyzed is gradually expanded/contracted and/or shifted within a predetermined allowable range, and the amount of expansion/contraction and/or the amount of shift where the correlation (similarity) between the peak waveform in the analysis target range in the data to be analyzed and the peak waveform in the corresponding range in the reference data is maximized is searched for.

When the above waveform correction is performed, the component peak determination part 18 is configured to compare the correlation between the component peak in the analysis target range in the data to be analyzed after the waveform correction is performed and the component peak in the corresponding range in the reference data with the determination criterion (threshold) retained in the determination criterion holding part 14, and determine that the component peak in the analysis target range and the component peak in the corresponding range in the reference data are identical to each other when the correlation satisfies the determination criterion.

The analysis target range for the waveform correction and the allowable range of expansion/contraction or shift of the peak waveform for the waveform correction can be arbitrarily designated by the user. The analysis target range designation part 22 is configured to require the user to arbitrarily designate the analysis target range for the waveform correction. The allowable range designation part 24 is configured to require the user to designate an allowable range of expansion/contraction or shift for the waveform correction.

The index value designation part 26 is configured to require the user to designate, by the separation index value, a component peak (reference component peak) whose presence is desired to be validated in the data to be analyzed. In other words, in this embodiment, the user can identify, by the separation index value, the component peak whose presence is desired to be validated in the data to be analyzed. When the user designates the separation index value of the component peak whose presence is desired to be validated in the data to be analyzed, the component peak determination part 18 determines whether the difference between the component-to-be-analyzed index value of the component peak in the data to be analyzed identified by the component-to-be-analyzed index value identification part 10 and the separation index value designated by the user satisfies the determination criterion.

The reference component name input part 28 is configured to require the user to arbitrarily input the component name of each component peak in the reference data. The component name of each component peak input by the user is displayed in determination result data output by a determination result output part 30 described later as a determination result by the component peak determination part 18.

The determination result output part 30 is configured to output the determination result by the component peak determination part 18 to a display device such as a liquid crystal display or a printer electrically connected to the analyzer 4.

Figure 2:
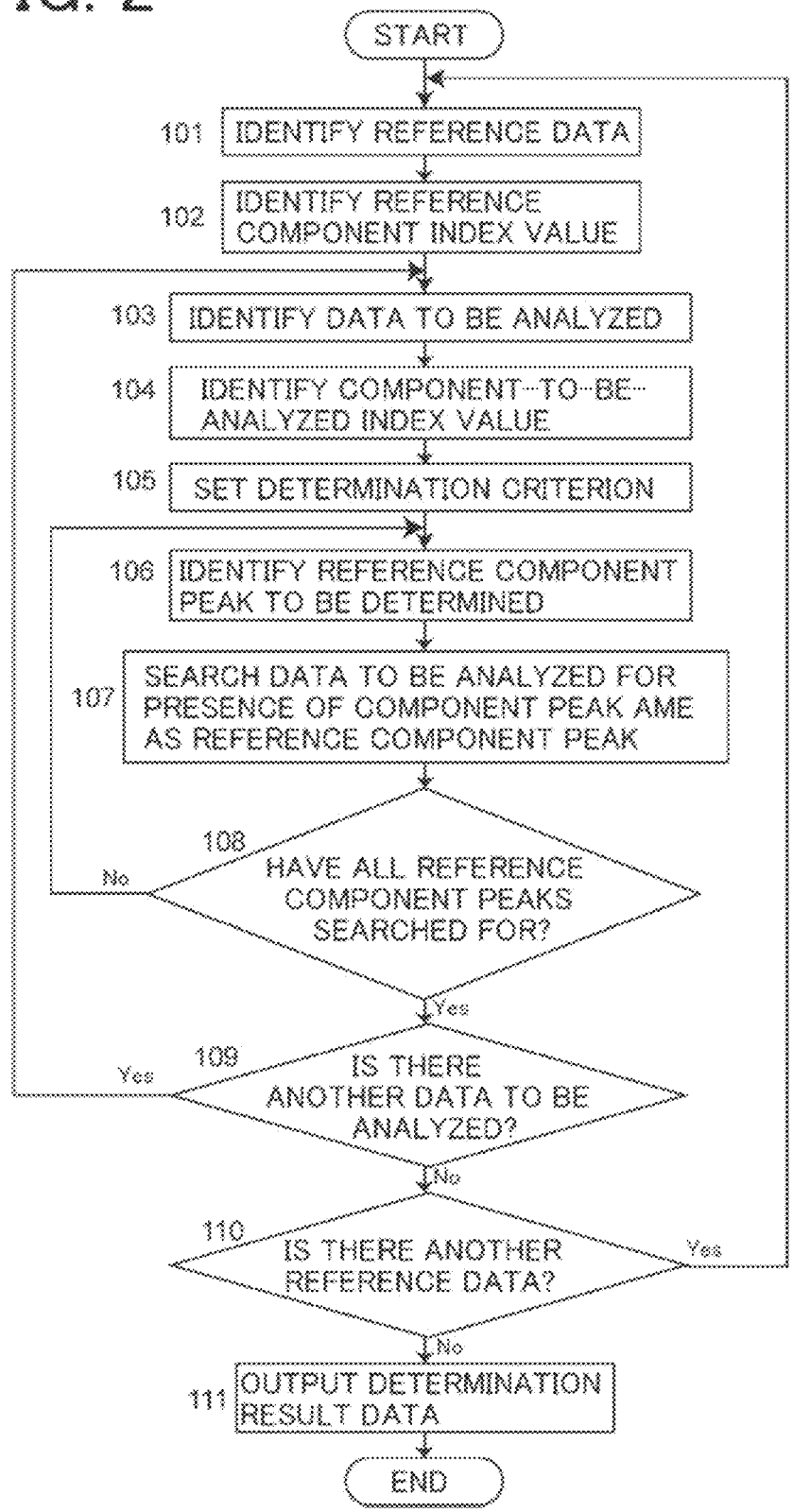
FIG. 2 is a flowchart showing an example of fingerprinting performed by the analyzer of the embodiment.

An example of the fingerprinting analysis operation using the separation index value of the component peak in the reference data will be described using the flowchart of FIG. 2 together with FIG. 1.

First, when the user identifies one of a plurality of pieces of separation data fetched into the analyzer 4 from the electrophoresis device 2 as reference data (step 101), the reference component index value identification part 12 identifies a separation index value (for example, time and size) of the component peak in the reference data as a reference component index value (step 102).

One piece of the separation data other than the reference data is set as the data to be analyzed (step 103), and the component-to-be-analyzed index value identification part 10 identifies, as the component-to-be-analyzed index value, the separation index value of the component peak in the data to be analyzed (step 104). The determination criterion input part 16 sets a determination criterion by causing the user to input a value serving as the determination criterion (step 105). Note that the determination criterion may be input and set at any stage before step 104.

One component peak (reference component peak) in the reference data to be determined whether it is present in the data to be analyzed is identified (step 106), the difference between the reference component index value of the reference component peak and the component-to-be-analyzed index value satisfies the determination criterion (for example, within ±5% of the reference component index value), and whether a component peak determined to be the component peak identical to the reference component peak is present in the data to be analyzed is searched for (step 107). The search result (present or not present) is temporarily stored in a storage area such as a flash memory. The operations in steps 106 to 107 are performed for all reference component peaks in the reference data (step 108). Thereby, the fingerprinting analysis for one piece of data to be analyzed is completed.

Figure 5:
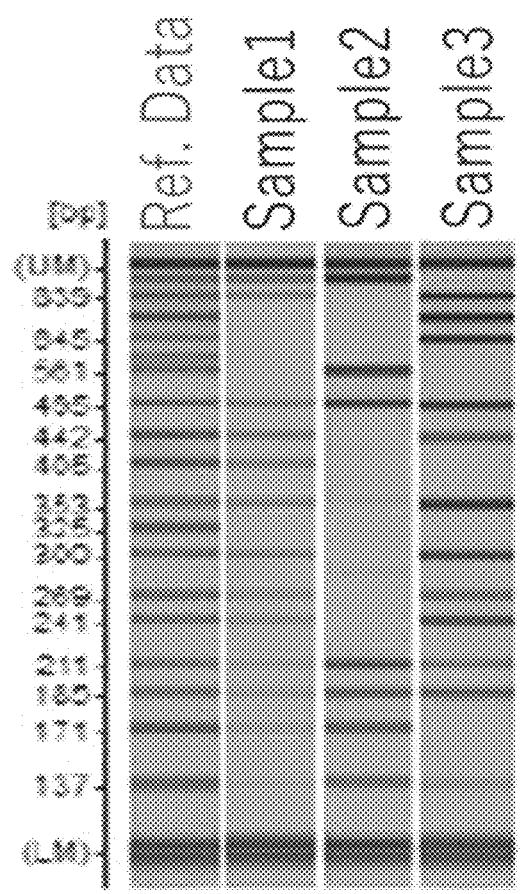
FIG. 5 is a diagram showing an example (gel image) of fingerprinting determination result data of the embodiment.

When there is a plurality of pieces of data to be analyzed, the fingerprinting analysis from steps 103 to 108 is performed on all the data to be analyzed (step 109). After completing the fingerprinting analysis for all the data to be analyzed, when the user desires to use another separation data as reference data (step 110), for new reference data, the fingerprinting analysis in steps 101 to 109 is performed. After completing the fingerprinting analysis using all the reference data desired by the user, the determination result output part 30 outputs the determination result data obtained by all the fingerprinting analysis (step 111). As shown in FIG. 5 as determination result data to be output, the data to be analyzed and reference data (Ref. Data) gel images are arranged side by side so that the component peaks present in the data to be analyzed (Samples 1 to 3) can be easily grasped visually. Further, as shown in FIG. 6, the determination result data may be a determination result table in which component peaks present in the data to be analyzed (Samples 1 to 3) are indicated by ○ or the like. Furthermore, both the gel image in FIG. 5 and the determination result table in FIG. 6 may be output.

When fingerprinting analysis is automatically performed using the determination criterion as described above, as shown in FIG. 7, fingerprinting analysis of separation data showing complex band patterns that are difficult to determine visually can be performed.

Here, when the separation index values of a plurality of reference component peaks are close to each other, the determination criteria for the reference component peaks may overlap each other. For example, when the fragment size (separation index value) of a certain reference component peak is 800 bp, and the fragment size of the reference component peak adjacent to it is 740, both determination criteria (±5%) are 760 bp to 840 bp and 703 bp to 777 bp respectively, and both determination criteria overlap between 760 bp and 777 bp. In such a case, when the fragment size of a certain component peak in the data to be analyzed is 765 bp, it is determined that this component peak is identical to both of the two reference component peaks.

Therefore, the component peak determination part 18 of this embodiment determines, when the separation index value of a certain component peak in the data to be analyzed is within the overlapping range of the determination criteria of a plurality of reference component peaks, that the component peak to be analyzed is identical to the reference component peak with the closest separation index value. In the above example, the fragment size 765 bp of the component peak in the data to be analyzed is closest to the reference component peak whose fragment size is 740 bp, so that the component peak is determined to be identical to the reference component peak whose fragment size is 740 bp.

When the peak determination part 18 makes the above determination, the determination result output part 30 issues, in the determination result to be output, a warning indicating that there is a plurality of reference component peaks that is capable of being determined to be identical to the component peak. Any warning may be used as long as the warning can be distinguished from a notation indicating that the peak is normally determined to be the identical component peak ("○" in FIG. 8), as indicated by "●" in Fragment No. 1 of Sample 2 in FIG. 8.

Figure 3:
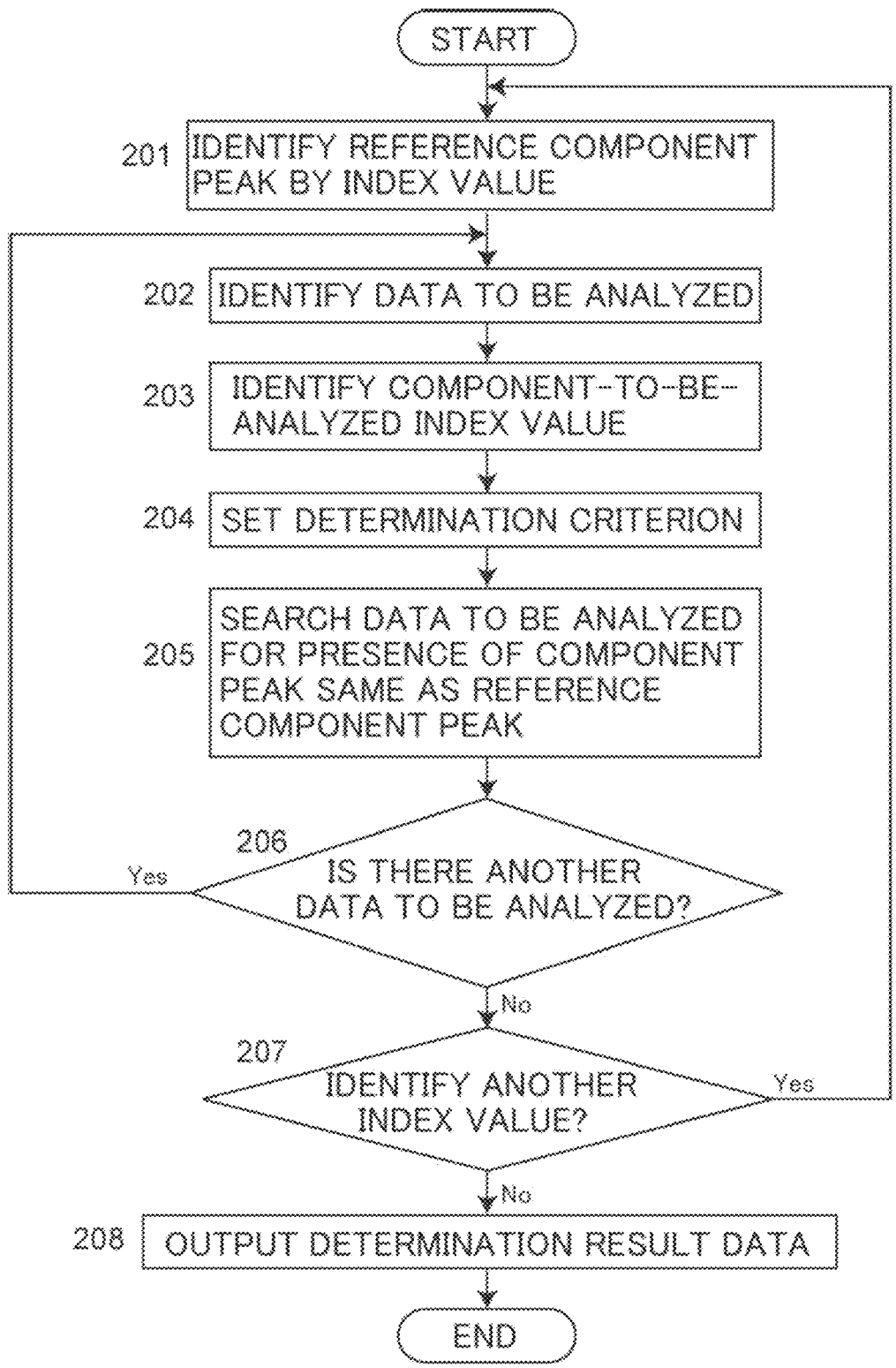
FIG. 3 is a flowchart showing another example of fingerprinting performed by the analyzer of the embodiment.

Next, an example of the fingerprinting analysis operation when the user identifies the reference component peak by the separation index value will be described using the flowchart of FIG. 3 together with FIG. 1.

When the separation index value of the reference component peak is identified by the user (step 201) and one piece of data to be analyzed is identified (step 202), the component-to-be-analyzed index value identification part 10 identifies the separation index value of the component peak in the data to be analyzed as the component-to-be-analyzed index value (step 203). The determination criterion input part 16 sets a determination criterion by causing the user to input a value serving as the determination criterion (step 204). Note that the determination criterion may be input and set at any stage before step 203.

Whether a component peak in which the difference between the reference component index value identified by the user and the component-to-be-analyzed index value satisfies a determination criterion (for example, within ±5% of the reference component index value) and that is determined to be the component peak identical to the reference component peak is present in the data to be analyzed is searched for (step 205). The search result (present or not present) is temporarily stored in a storage area such as a flash memory. When there is a plurality of pieces of data to be analyzed, the fingerprinting analysis from steps 202 to 205 is performed for all the data to be analyzed (step 206). After completing the fingerprinting analysis for all the data to be analyzed, when the user desires fingerprinting analysis using another index value (step 207), the processing of steps 201 to 206 is performed for the new index value. After performing all fingerprinting analysis using the index value desired by the user, the determination result output part 30 outputs determination result data (step 208).

Further, in the above case, the determination criteria for a plurality of reference component peaks may overlap each other. When the separation index value of a certain component peak in the data to be analyzed is within the overlapping range of determination criteria for multiple reference component peaks in such a case, the component peak determination part 18 determines that the component peak to be analyzed is identical to the reference component peak with the closest separation index value. When the peak determination part 18 makes such a determination, the determination result output part 30 issues, in the determination result to be output, a warning indicating that there is a plurality of reference component peaks that is capable of being determined to be identical to the component peak.

Figure 4:
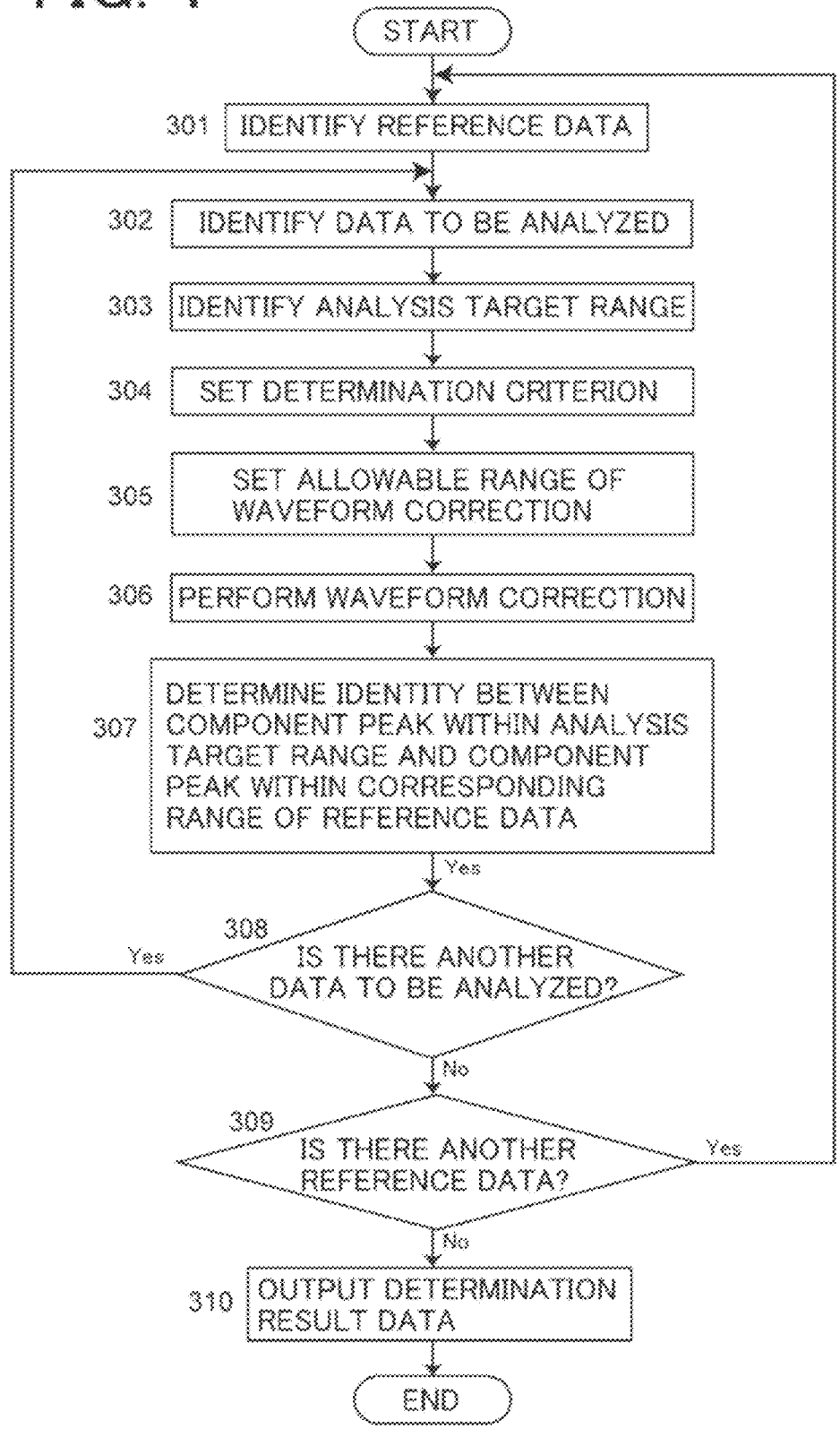
FIG. 4 is a flowchart showing still another example of fingerprinting performed by the analyzer of the embodiment.

Next, an example of the fingerprinting analysis operation when the waveform correction is performed will be described with reference to FIG. 1 together with the flowchart of FIG. 4.

When the user identifies, as reference data, any one of a plurality of pieces of separation data fetched from the electrophoresis device 2 into the analyzer 4 (step 301), one piece of the separation data other than the reference data is set as data to be analyzed (Step 302). The analysis target range designation part 22 causes the user to designate, as the analysis target range, any range in the data to be analyzed (Step 303). The determination criterion input part 16 sets a determination criterion by causing the user to input a value serving as the determination criterion (step 304). Note that the determination criteria may be input and set at any stage before step 303. Further, the allowable range designation part 24 causes the user to designate an allowable range for expanding/contracting and/or shifting the component peak of the analysis target range by the waveform correction (step 305). The designation of the allowable range may be performed at any stage before step 304.

The waveform correction is performed to expand/contract and/or shift the component peak in the analysis target range designated by the user within the allowable range designated by the user (step 306). In the waveform correction, the component peak in the analysis target range is expanded/contracted and/or shifted so that the correlation between the component peak in the analysis target range of the data to be analyzed and the component peak in the corresponding range of the reference data is maximized. The component peak determination part 18 determines the identity between the component peak within the analysis target range and the component peak within the corresponding range of the reference data based on whether the correlation of the component peak within the analysis target range after the waveform correction is performed satisfies the determination criterion (step 307).

Figure 7:
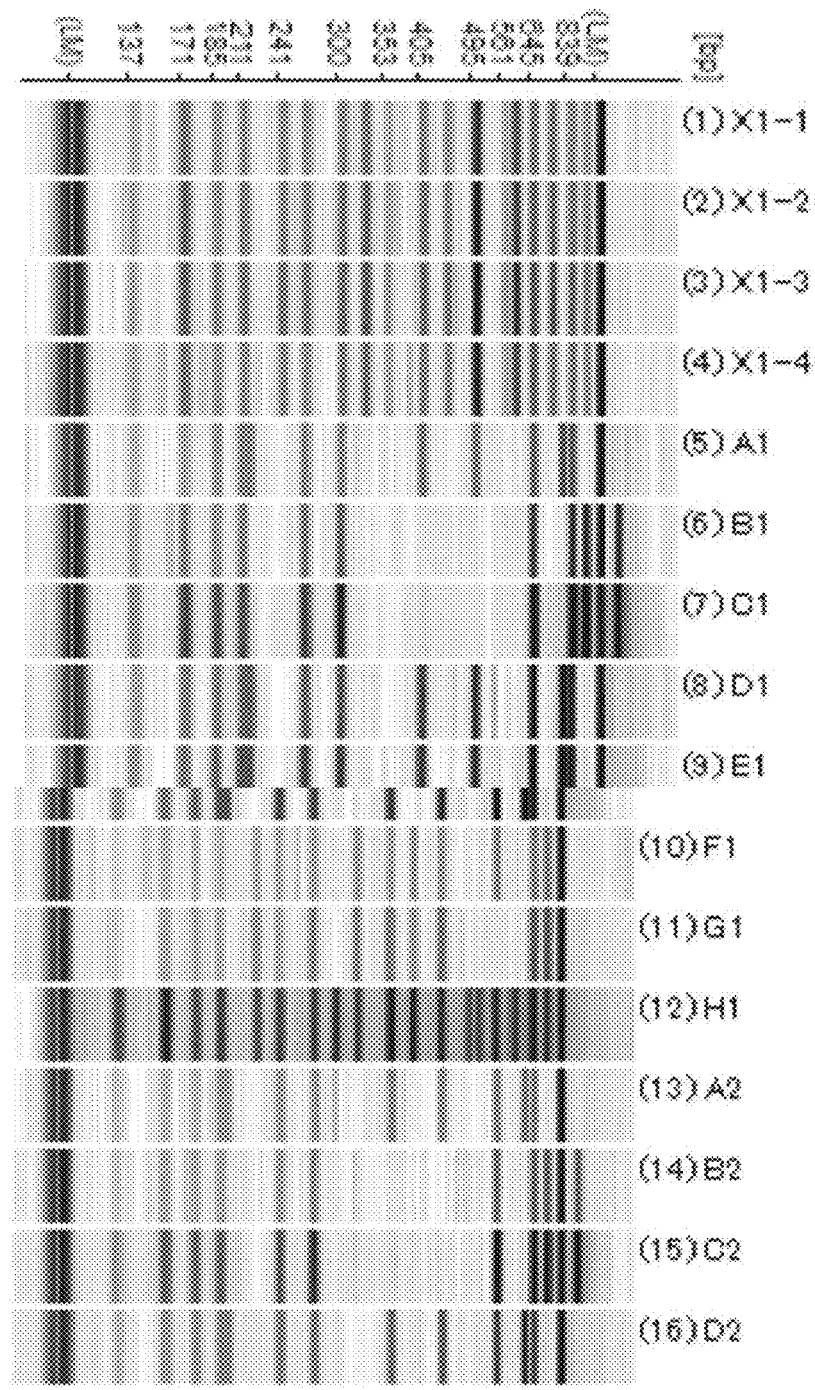
FIG. 7 is a diagram showing an example of complex fingerprinting determination result data (gel image) performed in the embodiment.

When there is a plurality of pieces of data to be analyzed, the waveform correction and fingerprinting analysis in steps 302 to 307 are performed for all the data to be analyzed (step 308). After completing waveform correction and fingerprinting analysis for all the data to be analyzed, when the user desires to use another separation data as reference data (step 309), for new reference data, the fingerprinting analysis in steps 301 to 308 is performed. After completing the fingerprinting analysis using all the reference data desired by the user, the determination result output part 30 outputs the determination result data obtained by all the fingerprinting analysis (step 310). The determination result data output here may be as shown in FIGS. 5 to 7.

In the above case as well, the determination criteria for a plurality of reference component peaks may overlap each other. When the separation index value of a certain component peak in the data to be analyzed is within the overlapping range of determination criteria for multiple reference component peaks in such a case, the component peak determination part 18 determines that the component peak to be analyzed is identical to the reference component peak with the closest separation index value. When the peak determination part 18 makes such a determination, the determination result output part 30 issues, in the determination result to be output, a warning indicating that there is a plurality of reference component peaks that is capable of being determined to be identical to the component peak.

DESCRIPTION OF REFERENCE SIGNS

2 Electrophoresis device
4 Analyzer
6 Separation data holding part
8 Reference data designation part
10 Component-to-be-analyzed index value identification part
12 Reference component index value identification part
14 Determination criterion holding part
16 Determination criterion input part
18 Component peak determination part
20 Waveform correction part
22 Analysis target range designation part
24 Allowable range designation part
26 Index value designation part
28 Reference component name input part
30 Determination result output part

What is claimed is:
1. An analyzer that analyzes separation data obtained by an electrophoresis analysis, the analyzer comprising:
a separation data holding part configured (i) to hold, as reference data, separation data obtained by an electrophoresis analysis of a reference sample including reference components which are known components and (ii) to hold, as testing data to be analyzed, separation data obtained by an electrophoresis analysis of a testing sample to be analyzed;
a determination criterion holding part configured to hold a determination criterion for determining whether component peaks in the reference data and component peaks in the testing data to be analyzed are identical;

a component peak determination part configured to determine whether the component peaks in the reference data and the component peaks in the testing data to be analyzed are identical respectively using the determination criterion; and an index value designation part configured to require a user to designate, using a separation index value, whether a particular designated component peak of the component peaks in the reference data is or is not present in the testing data to be analyzed, wherein the component peak determination part is configured to identify that a component peak of the component peaks in the testing data to be analyzed is identical to the particular designated component peak when a difference between the separation index value of the particular designated peak in the reference data and a component-to-be-analyzed index value of the component peak in the testing data to be analyzed satisfies the determination criterion of being identical or not identical;

wherein the analyzer further comprises a waveform correction part configured to normalize the testing data to be analyzed to reduce variation due to a difference in electrophoresis analysis conditions in the testing data to be analyzed by performing a step selected from a waveform correction to expand/contract and/or shift a peak waveform to obtain an analysis target range within a predetermined allowable range so that a correlation between the peak waveform in the analysis target range set in the testing data to be analyzed and the peak waveform in a range in the reference data corresponding to the analysis target range is maximized.

2. The analyzer according to claim 1, further comprising:

a component-to-be-analyzed index value identification part configured to identify, as component-to-be-analyzed index values, separation index value of component peaks in the testing data to be analyzed; and a reference component index value identification part configured to identify, as reference component index values, separation index values of component peaks in the reference data.

3. The analyzer according to claim 2, wherein the determination criterion is a difference allowance ratio that is a ratio of the difference between the component-to-be-analyzed index value and the reference component index value to the reference component index value.

4. The analyzer according to claim 1, wherein the component peak determination part is configured to identify, when a correlation between the peak waveform in the analysis target range after the waveform correction and the peak waveform in a range in the reference data corresponding to the analysis target range satisfies the determination criterion, that component peaks in the analysis target range in the testing data are identical to component peaks in the range in the reference data corresponding to the analysis target range in the testing data.

5. The analyzer according to claim 4, further comprising an analysis target range designation part configured to require a user to designate the analysis target range, wherein the waveform correction part is configured to perform the waveform correction on the analysis target range designated by a user.

6. The analyzer according to claim 4, further comprising a correction allowable range designation part configured to require a user to designate the predetermined allowable range, wherein the waveform correction part is configured to perform the waveform correction in the predetermined allowable range designated by a user.

7. The analyzer according to claim 1, further comprising a determination criterion input part configured to require a user to input the determination criterion, wherein the determination criterion holding part is configured to hold the determination criterion input by the user.

8. The analyzer according to claim 1, wherein the separation data holding part is configured to hold a plurality of pieces of separation data such that, to hold, as the reference data, one piece of the separation data, that is identified by a user, of the plurality of pieces of separation data, and to hold, as the testing data to be analyzed, at least one piece of remaining separation data.

9. An analyzer that analyzes separation data obtained by an electrophoresis analysis, the analyzer comprising:

a separation data holding part configured to hold, as reference data, separation data obtained by an electrophoresis analysis of a reference sample including reference components which are known components and to hold, as testing data to be analyzed, separation data obtained by an electrophoresis analysis of a testing sample to be analyzed;

a determination criterion holding part configured to hold a determination criterion for determining whether component peaks in the reference data and component peaks in the testing data to be analyzed are identical;

a component peak determination part configured to determine whether the component peaks in the reference data and the component peaks in the testing data to be analyzed are identical respectively using the determination criterion; and a reference component name input part configured to require a user to input names of the reference components;

a waveform correction part configured to normalize the testing data to be analyzed to reduce variation due to a difference in electrophoresis analysis conditions in the testing data to be analyzed by performing a step selected from a waveform correction to expand/contract and/or shift a peak waveform to obtain an analysis target range within a predetermined allowable range so that a correlation between the peak waveform in the analysis target range set in the testing data to be analyzed and the peak waveform in a range in the reference data corresponding to the analysis target range is maximized.

10. An analyzer that analyzes separation data obtained by an electrophoresis analysis, the analyzer comprising:

a separation data holding part configured to hold, as reference data, separation data obtained by an electrophoresis analysis of a reference sample including reference components which are known components and to hold, as testing data to be analyzed, separation data obtained by an electrophoresis analysis of a testing sample to be analyzed;

a determination criterion holding part configured to hold a determination criterion for determining whether component peaks in the reference data and component peaks in the testing data to be analyzed are identical;

a component peak determination part configured to determine whether the component peaks in the reference data and the component peaks in the testing data to be analyzed are identical respectively using the determination criterion; and wherein when there is a plurality of component peaks, in the reference data, that are capable of being determined using the determination criterion, the component peak determination part is configured to identify that one component peak, in the reference data, having a separation index value closest to a corresponding separation index value of the component peak in the testing data to be analyzed, is identical to the component peak in the testing data to be analyzed;

wherein the analyzer further comprises a waveform correction part configured to normalize the testing data to be analyzed to reduce variation due to a difference in electrophoresis analysis conditions in the testing data to be analyzed by performing a step selected from a waveform correction to expand/contract and/or shift a peak waveform to obtain an analysis target range within a predetermined allowable range so that a correlation between the peak waveform in the analysis target range set in the testing data to be analyzed and the peak waveform in a range in the reference data corresponding to the analysis target range is maximized.

11. The analyzer according to claim 10, further comprising a determination result output part configured to output a determination result by the component peak determination part, wherein the determination result output part configured to issue a warning in the determination result if the component peak determination part identifies that one component peak from among the plurality of component peaks, in the reference data, that are capable of being determined, is identical to the component peak in the testing data to be analyzed.

* * * * *